United States Patent [19]

Fussman

[11] Patent Number: 5,713,868
[45] Date of Patent: Feb. 3, 1998

[54] CATHETERIZATION DEVICE WITH DILATOR

[76] Inventor: Arie Fussman, 2 Manitou Falls Ter., Sparta, N.J. 07871

[21] Appl. No.: 811,497

[22] Filed: Mar. 5, 1997

[51] Int. Cl.⁶ ................................................ A61M 5/178
[52] U.S. Cl. .................................. 604/164; 604/191
[58] Field of Search ................................ 604/164, 166, 604/167, 174, 280, 282; 606/191, 194

[56] References Cited

U.S. PATENT DOCUMENTS

| | | | |
|---|---|---|---|
| 438,929 | 10/1890 | Knight | 606/191 |
| 672,377 | 4/1901 | Kearns | 606/191 |
| 876,775 | 1/1908 | Crittenden | 606/191 |
| 945,739 | 1/1910 | Baird | 606/191 |
| 2,717,600 | 9/1955 | Huber | 604/164 X |
| 3,539,034 | 11/1970 | Tafeen | 604/164 |
| 3,698,396 | 10/1972 | Katerndahl et al. | 604/164 |
| 3,714,945 | 2/1973 | Stanley | 604/164 |
| 3,742,958 | 7/1973 | Rundles | 604/164 |
| 4,236,520 | 12/1980 | Anderson | 606/191 X |
| 4,552,554 | 11/1985 | Gould et al. | 604/164 X |
| 4,842,585 | 6/1989 | Witt | 604/158 |
| 4,921,479 | 5/1990 | Grayzel | 604/53 |
| 5,057,083 | 10/1991 | Gellman | 604/164 |
| 5,246,424 | 9/1993 | Wilk | 604/164 |
| 5,304,142 | 4/1994 | Liebl et al. | 606/191 X |
| 5,330,499 | 7/1994 | Kanesaka | 606/191 X |
| 5,380,290 | 1/1995 | Makower et al. | 604/164 |
| 5,405,341 | 4/1995 | Martin | 604/164 X |

*Primary Examiner*—Sam Rimell
*Attorney, Agent, or Firm*—David L. Davis

[57] ABSTRACT

A two part plastic catheterization device wherein the forward end of the device acts as a dilator and has an offset axial opening along one side for a relatively small needle to pass through. The rear of the device has a lumen for holding a catheter and the lumen is closed by a slidable cover member. The forward end of the lumen is terminated by a slanted guide wall and the forward end of the cover member is resiliently flexible to engage a recess in the guide wall to retain the cover member when it closes the lumen. This device eliminates the need for a separate guidewire and allows the use of a small diameter needle to minimize damage to the blood vessel wall. In an alternate embodiment, the cover member fills substantially the entire lumen and includes a longitudinal slot for holding a guidewire.

8 Claims, 4 Drawing Sheets

5,713,868

CATHETERIZATION DEVICE WITH DILATOR

BACKGROUND OF THE INVENTION

This invention relates to the insertion of a catheter into a blood vessel and, more particularly, to an improved device for both dilating a needle puncture in the blood vessel and for subsequently providing a guide for the insertion of a catheter into the blood vessel.

Vascular dilators are commonly used when inserting a catheter into a blood vessel in order to widen the hole formed by the initial needle or scalpel puncture so that the use of the dilator gradually enlarges the hole. In a typical procedure, a hollow needle is percutaneously inserted into the blood vessel and an elongate, slender guide member, such as a guidewire, is advanced through the interior of the hollow needle into the blood vessel. The needle is then removed over the guide member, leaving the guide member in place in the blood vessel and extending proximally out of and through the patient's skin. The hole left by the needle in the blood vessel typically is too small to permit the catheter to be passed therethrough. A dilator is provided to widen the hole. Dilators commonly are in the form of a flexible plastic tube having a guide member lumen adapted to be passed over the guide member. The dilator is of uniform wall thickness except for a distal portion which tapers in a distal direction to the circular distal outlet opening at the distal end of the dilator. The wall thickness of the dilator at the distal tip is relatively thin to facilitate its entry into the hole made by the needle. As the dilator is advanced over the guide member through the puncture hole, the tapered distal portion presents a progressively wider diameter to the puncture hole, thus gradually enlarging the hole. The catheter may be mounted on and carried by the dilator so that once the dilator has been inserted to its full diameter into the blood vessel, the catheter then may be advanced over the dilator and through the enlarged puncture hole into the blood vessel. The dilator and guide member then may be withdrawn, leaving the percutaneously placed catheter in place in the blood vessel. This procedure possesses a number of disadvantages. For example, a relatively large needle for accommodating the guide member therein is required to penetrate the wall of the blood vessel. Also, a disposable guide member is required.

It would therefore be desirable to provide a catheterization device wherein only a relatively small diameter needle is utilized and no separate guide member is needed.

SUMMARY OF THE INVENTION

According to the present invention, a catheterization device is constructed in which a relatively small needle is utilized and no separate guide member is needed. The inventive catheterization device comprises a unitary dilator member and an elongated cover member. The dilator member has an elongated body portion with an outer wall defining a substantially uniform first lumen open at the rear end of the body portion and adapted for receiving a catheter therein. The body portion has an elongated opening longitudinally disposed in the outer wall communicating with the first lumen from a forward end of the elongated opening to the rear end of the body portion. The forward end of the first lumen is terminated by a guide wall extending from the bottom of the first lumen opposite the elongated opening and ascending obliquely toward the forward end of the elongated opening. At least a forward portion of the elongated opening is large enough to allow the catheter to pass therethrough.

The dilator member further has a forward portion extending forwardly of the guide wall and tapering inwardly to a front tip. The forward portion has a second lumen therein which extends rearwardly from the front tip to a lateral opening. The second lumen is adapted for receiving a hypodermic syringe needle therein with the tip of the needle extending forwardly of the front tip and the syringe extending rearwardly alongside the dilator member body portion. The cover member is slidable forwardly and rearwardly along the elongated opening of the body portion. The cover member closes the first lumen when moved toward the front tip and exposes the first lumen when moved away from the front tip.

In accordance with an aspect of this invention, the second lumen is tapered inwardly toward the front tip.

In accordance with another aspect of this invention, the guide wall is formed with a recess below the forward end of the elongated opening and the cover member has a forward end adapted to be received in the recess. The cover member is formed with a weakened portion extending laterally thereacross to act as a resilient hinge and enable the cover member forward end to be resiliently flexed downwardly for receipt in the recess of the guide wall.

In accordance with a further aspect of this invention, a substantial portion of the length of the body portion forwardly from its rear end is substantially cylindrical and the forward portion of the dilator member extends beyond an axial projection of the cylindrical body portion. At least the lateral opening of the second lumen is in that part of the forward portion which extends beyond the axial projection.

BRIEF DESCRIPTION OF THE DRAWINGS

The foregoing will be more readily apparent upon reading the following description in conjunction with the drawings in which like elements in different figures thereof are identified by the same reference numeral and wherein.

DETAILED DESCRIPTION

Figure 1:
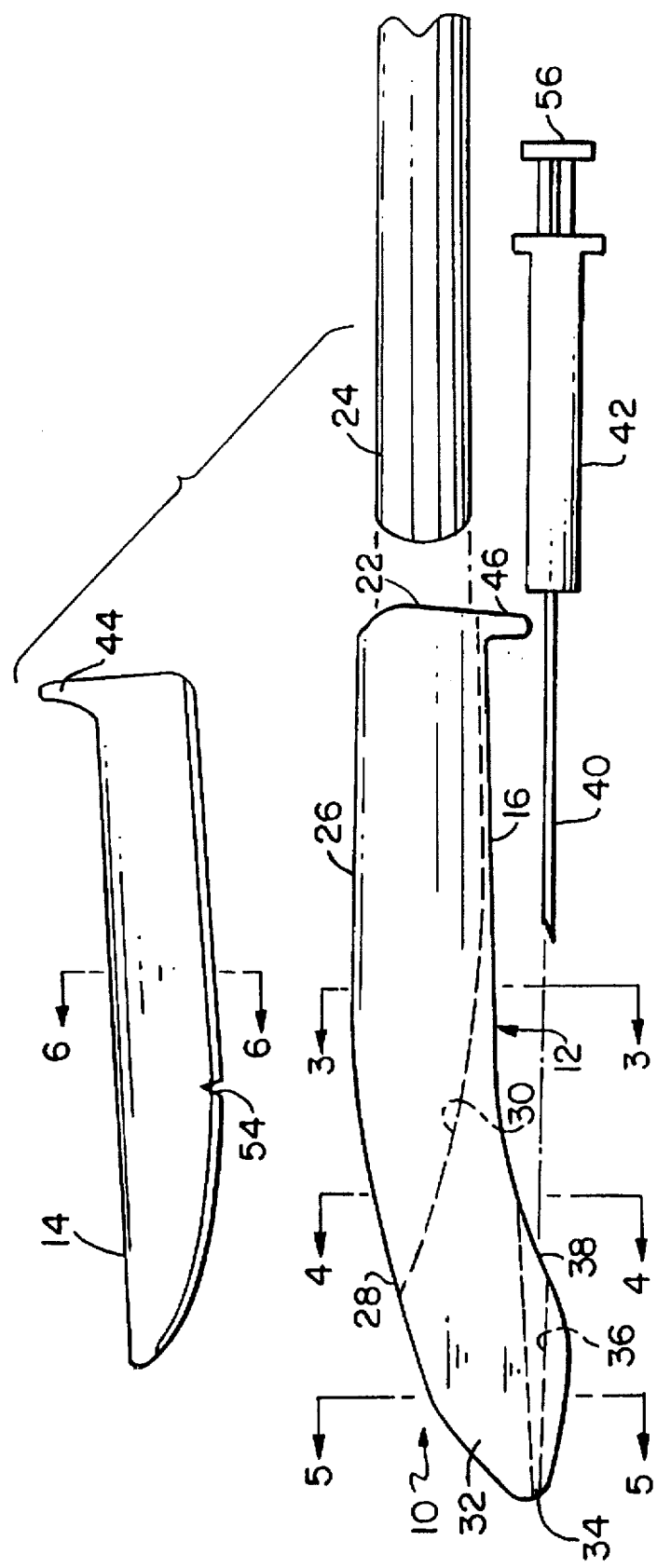
FIG. 1 is an exploded side view showing a catheterization device according to this invention, along with a hypodermic syringe needle and a catheter.

Referring now to the drawings, the catheterization device according to the present invention, designated generally by the reference numeral 10, comprises a dilator member 12 and a cover member 14. The dilator member 12 is of unitary construction and preferably is formed of a plastic material by a molding process. Similarly, the cover member 14 is also of unitary construction and preferably is formed of a plastic material by a molding process.

Figure 2:
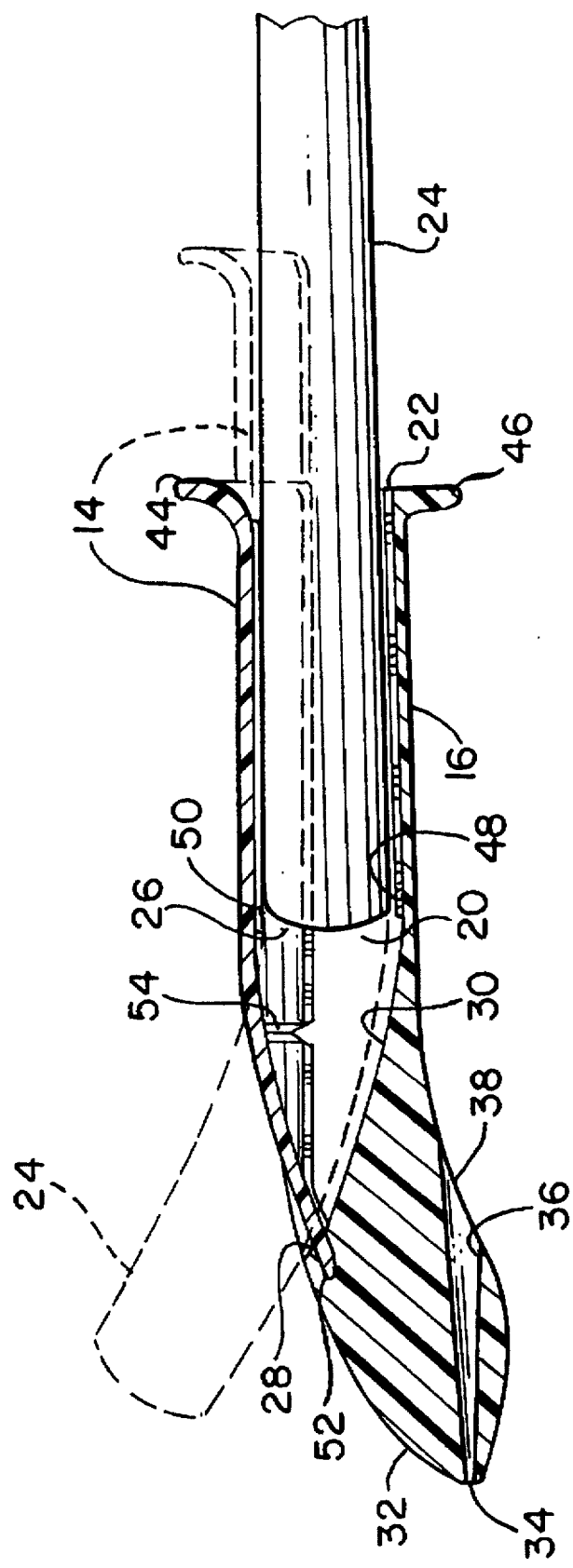
FIG. 2 is a longitudinal cross section of the catheterization device according to this invention showing, in solid lines, the catheter inserted in the device and, in broken lines, the guiding of the catheter out of the device.

The dilator member 12 has an elongated body portion 16 having an outer wall 18 which defines a substantially uniform first lumen 20 which is open at the rear end 22 of the body portion 16. The first lumen 20 is adapted for receiving a catheter 24 therein, as best shown in FIG. 2. The body portion 16 has an elongated opening 26 longitudinally disposed in the outer wall 18 which communicates with the first lumen 20 from a forward end 28 of the opening 26 to the rear end 22 of the body portion 16. As will become clear from the following discussion, at least a forward portion of the elongated opening 26 is of sufficient size to allow the catheter 24 to pass therethrough.

Figure 3:
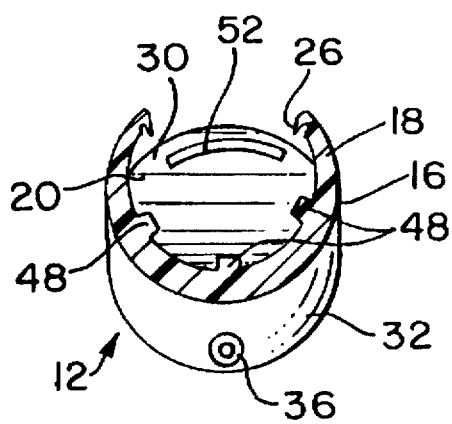
FIG. 3 is a cross sectional view of the dilator member taken along the line 3—3 in FIG. 1.
Figure 4:
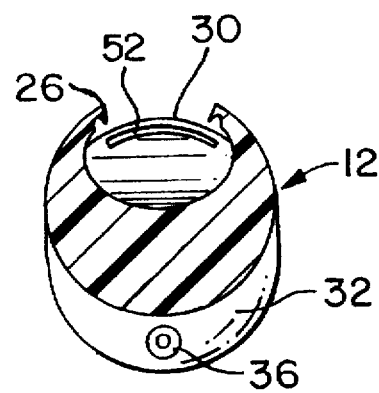
FIG. 4 is a cross sectional view of the dilator member taken along the line 4—14 in FIG. 1.
Figure 5:
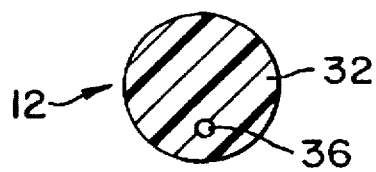
FIG. 5 is a cross sectional view of the dilator member taken along the line 5—5 in FIG. 1.

The forward end of the first lumen 20 is terminated by a guide wall 30 which extends from the bottom of the first lumen 20 opposite the elongated opening 26 and ascends obliquely toward the forward end 28 of the elongated opening 26. A substantial portion of the length of the body portion 16, illustratively from the rear end 22 to the bottom of the guide wall 30, is substantially cylindrical, except for the opening 26. Beginning at the guide wall 30, the dilator member 12 has a forward portion 32 which extends forwardly of the guide wall 30 and tapers inwardly to a front tip 34. This forward portion 32 extends to the opposite side of the dilator member 12 from the elongated opening 26 beyond an axial projection of the cylindrical part of the body portion 16, as is clear from FIG. 3. The forward portion 32 is formed with a second lumen 36 which extends rearwardly from the front tip 34 to a lateral opening 38 on the opposite side of the dilator member 12 from the elongated opening 26. The second lumen 36 is adapted for receiving therein the needle 40 of a hypodermic syringe 42, with the tip of the needle 40 extending forwardly of the front tip 34 and the syringe 42 extending rearwardly alongside the body portion 16 of the dilator member 12. Preferably, the second lumen 36 is tapered inwardly toward the front tip 34 so that there is some freedom of movement between the needle 40 and the dilator member 12 when the dilator member 12 is manipulated for insertion into a blood vessel.

Figure 6:
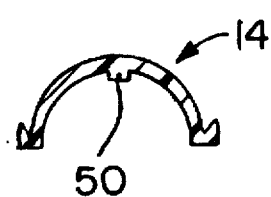
FIG. 6 is a cross sectional view of the cover member taken along the line 6—6 in FIG. 1.
Figure 8:
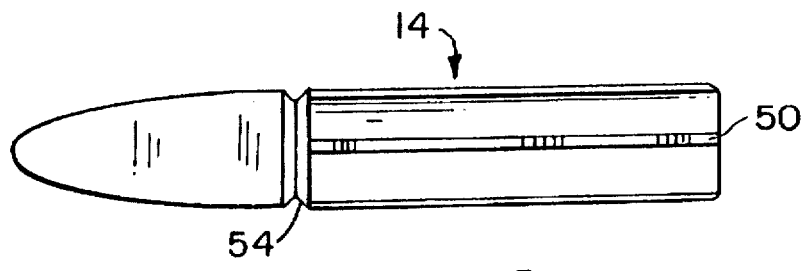
FIG. 8 is a bottom plan view of the cover member.

The cover member 14 of the catheterization device 10 cooperates with the dilator member 12 so as to be slidable forwardly and rearwardly along the elongated opening 26. Thus, the cover member 14 closes the first lumen 20 when it is moved toward the front tip 34 and exposes the first lumen 20 when it is moved away from the front tip 34. The cover member 14 is curved so as to be a partial cylinder, as best shown in FIG. 6. At its rear end, the cover member 14 is formed with an outwardly extending flange 44 and the dilator member 12 is similarly formed with an outwardly extending flange at its rear end 22. The flanges 44, 46 function as handles to aid in manipulating the catheterization device 10, as will become clear from the following discussion. Although the flanges 44, 46 are shown as being oriented diametrically opposite each other, it is understood that other configurations may be utilized as well.

The outer wall 18 is preferably formed with at least one longitudinally extending rib 48 along its inner surface within the first lumen 20 and the cover member 14 is formed with at least one longitudinally extending rib 50 along its inner surface which extends into the first lumen 20 when the cover member 14 is positioned on the body portion 16 to close the first lumen 20. The ribs 48, 50 provide a sliding surface for the catheter 24 to minimize the surface contact area of the catheter 24 on the catheterization device 10 in order to reduce sliding friction.

The guide wall 30 is formed with a recess, or notch, 52 below the forward end 28 of the elongated opening 26. The configuration of the recess 52 and the shape of the forward end of the cover member 14 are such that the forward end of the cover member 14 can be received in the recess 52 when the cover member 14 is moved forwardly and downwardly to close the first lumen 20. However, as is clear from FIG. 2, the recess 52 is aligned with the catheter 24 so that if the cover member 14 were to have its forward end permanently displaced downwardly to fit in the recess 52, when the cover member 14 was slid rearwardly to expose the first lumen 20, its forward end would drag against the catheter 24 and pull it out of the device 10, which is unacceptable. Accordingly, the cover member 14 is formed with a weakened portion 54 which extends laterally across the cover member 14 to act as a resilient hinge and enable the forward end of the cover member 14 to be resiliently flexed downwardly for receipt in the recess 52 of the guide wall 30. Alternatively, the cover member could be formed of a soft resilient plastic which curves downwardly at its forward end. In such case, the recess 52 would not be necessary and the cover member would lightly graze the top of the catheter when it is retracted.

Figure 7:
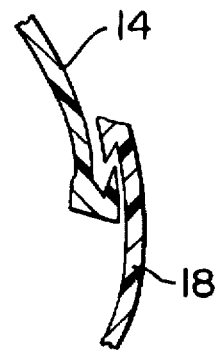
FIG. 7 is a cross sectional detail showing the interlocking of the cover member with the dilator member.

To enable the cover member 14 to readily slide along the dilator member 12 and still be held in the proper angular orientation, it is preferred that interlocking features, such as are shown in FIG. 7, be provided at the ends of the cover member 14 and the outer wall 18.

In use, the cover member 14 is slid forwardly along the dilator member 12 and its forward end is flexed downwardly for receipt within the recess 52. The needle 40 is then inserted through the second lumen 36 and is used to puncture the patient's skin and blood vessel. The plunger 56 of the syringe 42 is then withdrawn to draw blood from the blood vessel in order to insure that the needle 40 has actually punctured same. By pressing forward on the flanges 44, 46, the front tip of the forward portion 32 is used to dilate the puncture made by the needle 40 and the catheterization device 10 is inserted into the blood vessel for a substantial portion of its length, with the cover member 14 keeping the first lumen 20 closed. The tapered form of the second lumen 36 allows the dilator member 12 to be manipulated relative to the needle 40 during the insertion, so as not to break the fragile needle 40. The catheter 24 is then inserted into the first lumen 20 from the rear end 22 of the dilator member 12, as shown by the solid lines in FIG. 2. The cover member 14 is then slid rearwardly, by gripping the flange 44, to expose the first lumen 20. As the forward end of the cover member 14 exits the recess 52, it snaps upwardly so that it passes over the catheter 24 without dragging it out of the catheterization device 10. The catheter 24 is then pushed forwardly and the guide wall 30 guides it out of the catheterization device 10 at an angle, as shown by the broken lines in FIG. 2. After a sufficient length of the catheter is inserted into the blood vessel, the dilator member 12 may be withdrawn from the blood vessel, by pulling on the flange 46. The catheter 24 may then be removed laterally from the dilator member 12 through the elongated opening 26.

Figure 9:
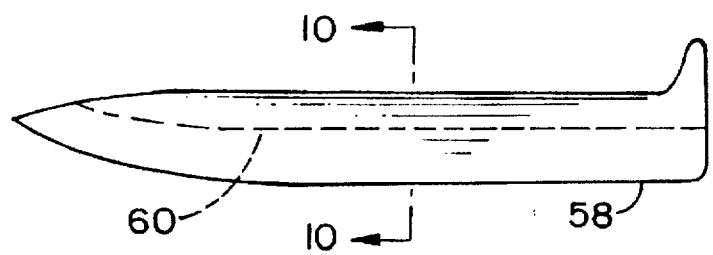
FIG. 9 is a side view of an alternate embodiment of a cover member for use when inserting a guidewire into a blood vessel.
Figure 10:
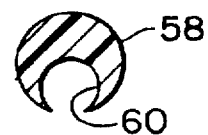
FIG. 10 is a cross sectional view of the alternate embodiment cover member taken along the line 10—10 in FIG. 9.
Figure 11:
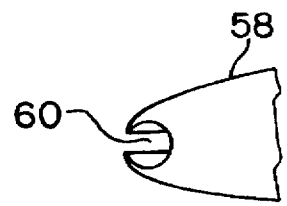
FIG. 11 is a top plan view of the forward portion of the cover member shown in FIG. 9.

There are times when it is desired to be able to insert a guidewire into a blood vessel. For example, in an angiography procedure, a guidewire is inserted into an artery and advanced through the artery toward the heart. For such a procedure, the cover member 58 (FIGS. 9-11) is used with the dilator member 12. As shown, the cover member 58 fills substantially the entire first lumen 20 and is formed with a third lumen 60 for accepting a guidewire therein. The third lumen 60 is open to the bottom of the cover member 58 and is open at both the front and rear ends of the cover member 58. The forward end of such a guidewire is typically bent into a J-shape and the catheterization device with such a guidewire would be packaged with the forward end of the guidewire extending through the open front end of the cover member 58. For insertion of the catheterization device into the artery, the guidewire would initially be pulled back slightly so that its forward end is straightened out and retained within the third lumen 60. After insertion of the catheterization device into the blood vessel, advancing of the guidewire out of the catheterization device results in the forward end returning to its J-shape.

Accordingly, there has been disclosed an improved device for both dilating a needle puncture in a blood vessel and for subsequently providing a guide for the insertion of a catheter into the blood vessel. This device eliminates the need for a disposable guidewire and also allows the use of a relatively small needle, thereby minimizing damage to the wall of the blood vessel. While alternate embodiments of the present invention have been disclosed herein, it will be apparent to one of ordinary skill in the art that various modifications and adaptations to the disclosed embodiments are possible and it is intended that this invention be limited only by the scope of the appended claims. For example, the cover member could extend outside the dilator member, instead of inside as shown. Also, the elongated opening of the dilator member could be along its bottom or side and, in such case, the cover member would be below or on the side of, respectively, the dilator member.

What is claimed is:

1. A catheterization device comprising:

a unitary dilator member having an elongated body portion with an outer wall defining a substantially uniform first lumen open at the rear end of the body portion and adapted for receiving a catheter therein, the body portion having an elongated opening longitudinally disposed in said outer wall communicating with said first lumen from a forward end of the elongated opening to the rear end of the body portion with at least a forward portion of the elongated opening being of sufficient size to allow the catheter to pass therethrough, the forward end of said first lumen being terminated by a guide wall extending from the bottom of the first lumen opposite the elongated opening and ascending obliquely toward the forward end of the elongated opening, the dilator member further having a forward portion extending forwardly of said guide wall and tapering inwardly to a front tip, the forward portion having a second lumen therein extending rearwardly from said front tip to a lateral opening, said second lumen adapted for receiving a hypodermic syringe needle therein with the tip of the needle extending forwardly of the front tip and the syringe extending rearwardly alongside the dilator member body portion; and an elongated cover member slidable forwardly and rearwardly along said body portion elongated opening, said cover member closing said first lumen when moved toward said front tip and exposing said first lumen when moved away from said front tip.

2. The catheterization device according to claim 1 wherein said second lumen is tapered inwardly toward said front tip.

3. The catheterization device according to claim 1 wherein said guide wall is formed with a recess below the forward end of said elongated opening and said cover member has a forward end adapted to be received in said recess, said cover member being formed with a weakened portion extending laterally across said cover member to act as a resilient hinge and enable said cover member forward end to be resiliently flexed downwardly for receipt in said guide wall recess.

4. The catheterization device according to claim 1 wherein:

said dilator member body portion is formed with a flange extending outwardly from said outer wall adjacent said body portion rear end to act as a handle for inserting said device into a blood vessel and for retracting said dilator member from said blood vessel; and said cover member is formed with an outwardly extending flange at its end opposite its forward end to act as a handle for inserting said device into said blood vessel and for retracting said cover member to expose said first lumen.

5. The catheterization device according to claim 1 wherein:

said body portion outer wall is formed with at least one longitudinally extending rib along its inner surface within said first lumen.

6. The catheterization device according to claim 5 wherein:

said cover member is formed with at least one longitudinally extending rib along its inner surface extending into said first lumen when said cover member is positioned on said body portion to close said first lumen.

7. The catheterization device according to claim 1 wherein a substantial portion of the length of said body portion forwardly from its rear end is substantially cylindrical and said forward portion of said dilator member extends beyond an axial projection of the cylindrical body portion, at least the lateral opening of said second lumen being in that part of said forward portion which extends beyond said axial projection.

8. The catheterization device according to claim 7 wherein said forward portion of said dilator member extends to the opposite side of said dilator member from said elongated opening.

* * * * *